United States Patent [19]

Morris

[11] Patent Number: 4,847,407
[45] Date of Patent: Jul. 11, 1989

[54] DIPHENYL ESTER DERIVATIVE OF STILBENEDICARBOXYLIC ACID

[75] Inventor: John C. Morris, Kingsport, Tenn.

[73] Assignee: Eastman Kodak Company, Rochester, N.Y.

[21] Appl. No.: 244,878

[22] Filed: Sep. 15, 1988

Related U.S. Application Data

[62] Division of Ser. No. 105,416, Oct. 7, 1987, Pat. No. 4,789,755.

[51] Int. Cl.$^4$ .......................................... C07C 69/773
[52] U.S. Cl. ...................................... 560/86; 560/76; 560/77; 562/488
[58] Field of Search .......................................... 560/86

[56] References Cited

U.S. PATENT DOCUMENTS

| | | | |
|---|---|---|---|
| 2,610,191 | 9/1952 | Toland | 562/411 X |
| 2,677,703 | 5/1954 | Toland | 562/488 |
| 2,688,631 | 9/1954 | Toland | 562/411 X |
| 3,548,018 | 12/1970 | Bhasin et al. | 585/415 |
| 3,953,498 | 4/1976 | Hartle | 560/80 |

*Primary Examiner*—Werren B. Lone
*Assistant Examiner*—Vera C. Clarke
*Attorney, Agent, or Firm*—Thomas R. Savitsky; William P. Heath, Jr.

[57] ABSTRACT

Disclosed are phenyl esters of stilbenedicarboxylic acid. The carboxylate portions of the compounds are bonded at the meta or para positions of the stilbene moiety.

2 Claims, No Drawings

DIPHENYL ESTER DERIVATIVE OF STILBENEDICARBOXYLIC ACID

This is a divisional of application Ser. No. 07/105,416, filed 10/7/87, now U.S. Pat. No. 4,789,755.

FIELD OF THE INVENTION

The present invention concerns a one-step process for preparing dimethyl or novel diphenyl derivatives of stilbenedicarboxylic acid.

BACKGROUND OF THE INVENTION

Ester derivatives of stilbenedicarboxylic acid, such as dimethyl trans-4,4'-stilbenedicarboxylate (DMSDC) and diphenyl trans-4,4'-stilbenedicarboxylate (DPSDC), are useful building blocks for high performance polyester engineering plastics. In particular, a diphenyl ester derivative of stilbenedicarboxylic acid can be transesterified with bisphenol A to form a high molecular weight polyester which is useful as an engineering plastic.

The formation of stilbenes from substituted toluene has been reported by Toland and co-workers (see W. G. Toland, Jr., J. B. Wilkes, and F. J. Brutschy, J. Am. Chem. Soc., 75, 2263 (1953); W. G. Toland, Jr., and J. B. Wilkes, J. Am. Chem. Soc., 76, 307 (1954); U.S. Pat. Nos. 2,610,191; 2,677,703; and 2,688,631).

In these references it was shown that the free carboxylic acid and cyano derivatives of toluene could be converted to stilbenes under particular conditions. It has also been shown that unsubstituted toluene can be converted to stilbene (see Aronstein and Van Nierop, Rec. Trav. Chim., 21, 488 (1902); Friedman, Ber., 49, 277,1334, 1352, 1551 (1902); and U.S. Pat. No. 3,548,018).

The dimethyl ester derivative of trans 4,4'-stilbenedicarboxylic acid has been reported to have been prepared from methyl p-toluate and sulfur [W. J. Jackson and J. C. Morris, Journal of Applied Polymer Science: Applied Polymer Symposium 41, 307–326 (1985)]; however, the efficacy of efficient removal of hydrogen sulfide and enhancement of yield by careful attention to the high molar ratio of methyl p-toluate to sulfur in this reaction have heretofore been unknown.

SUMMARY OF THE INVENTION

The present invention is directed to a process for preparing dimethyl or diphenyl derivatives of stilbenedicarboxylic acids using particular molar ratios of reactants and under conditions wherein the hydrogen sulfide formed during the reaction is removed. More particularly, the present invention is directed to a process for preparing an ester compound of the formula:

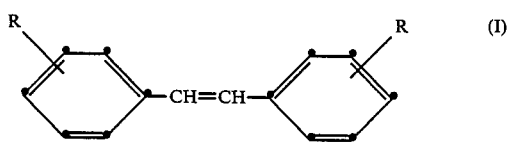

wherein R is bonded at the meta or para positions and is a group of the formula —COOR' wherein R' is methyl or phenyl, comprising reacting a compound of the formula:

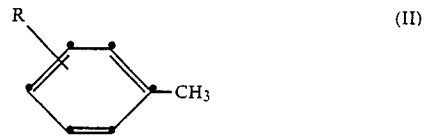

wherein R is as defined hereinabove,
with elemental sulfur,
wherein Compound II is intially present at a molar excess relative to sulfur of at least about 5:1, and hydrogen sulfide produced during the reaction is removed from the reaction zone, said process occurring under an inert atmosphere and under reaction conditions such that Compound I is formed. It is preferred that the R moieties of Compound I and Compound II are bonded at the para positions. When the R' moieties of Compound I are phenyl, such compounds are novel and are also within the scope of the present invention.

DETAILED DESCRIPTION OF THE INVENTION

The process of the present invention is preferably carried out using neat Compound II or, optionally, a suitable solvent can be used. Suitable solvents include diphenyl ether, dimethyl phthalate, biphenyl, and the like.

In carrying out the process of the present invention, an appropriate bibenzyl derivative is typically formed (as used herein "bibenzyl derivative" or "bibenzyl" refers to a dimethyl bibenzyldicarboxylate derivative and/or a diphenyl bibenzyldicarboxylate derivative). It is desirable to increase the rate of Compound I relative to the amount of bibenzyl derivative formed. Even though the bibenzyl derivative can be relatively easily converted to the desired Compound I by dehydrogenation with sulfur (further explained hereinafter), such additional conversion adds to the cost and time requirements. It has been found that the ratio of Compound I relative to bibenzyl derivative is substantially increased when the hydrogen sulfide (also produced during the reaction) is removed from the reaction zone. The more rapid the removal of hydrogen sulfide from the reaction zone, the higher the ratio of Compound I to bibenzyl derivative which is produced. Therefore, removal of the hydrogen sulfide at substantially the same rate that it is produced is most desirable. Such a rate of removal can be accomplished by continually sweeping the reaction zone with an inert gas such as nitrogen or argon.

The process of the present invention is typically carried out at a temperature of 230° C. to 320° C.; preferably 245° C. to 285° C. At temperatures below 230° C., the reaction is slower and may not be commercially feasible, and above 320° C. some decomposition may occur which results in lower yield and poor color.

The reaction time for the process of the present invention is typically from about 2 to about 6 hours, preferably from about 3 to about 4 hours. The pressure required for the process of the invention can vary from about atmospheric to about 250 pounds per square inch gauge (psig) depending upon the particular reactants and other reaction conditions. When using methyl p-toluate to form dimethyl trans 4,4'-stilbenedicarboxylate (DMSDC), at least about 50 psig is required. When R' of Compound I and Compound II is phenyl, the reaction can be carried out at atmospheric pressure thereby eliminating the need for costly pressurized equipment.

The initial molar ratios of reactants for the process of the invention are critical. An initial molar excess of Compound II of at least about 5:1 relative to sulfur is required to obtain satisfactory yield; preferred is at least about a 10:1 molar excess. The upper limit of the excess of Compound II is not critical and the only constraint on the upper limit is that of praticality and economics. A most preferred initial molar ratio of Compound II:-sulfur is between about 5:1 and about 20:1. After the initial ratios of reactants are allowed to react, the excess of Compound II becomes greater and greater as the sulfur is being consumed. The reaction typically proceeds until the sulfur is exhausted. Therefore an initial ratio of Compound II:sulfur of 5:1 results in about a 20% conversion of Compound II. Since the bibenzyl derivative can be easily converted to the desired Compound I, the combined yields of bibenzyl derivatives plus Compound I are important (as well as the yield of Compound I alone). Reactant ratios of Compound II to sulfur less than about 5:1 result in increased formation of other by-products that cannot as easily be converted to the desired Compound I, and therefore such ratios are undesirable.

In another embodiment of the present invention the appropriate bibenzyl derivative (formed with Compound I) is reacted with elemental sulfur in the presence of a suitable solvent such as diphenyl ether to form Compound I. Suitable conditions for this reaction are a temperature of from about 240° C. to about 300° C., a pressure of from about 10 to about 100 psig, a reaction period of from about 1 to about 24 hours, and with an inert gas sparge such as with nitrogen or argon.

In a preferred process of the invention methyl p-toluate is placed in a steel reactor with a magnetic stirrer and fittings so configured that nitrogen can be sparged into a reaction mixture of the bottom, passed through a condenser at the top of the reactor and allowed to escape through a pressure-dropping orifice so that a pressure of 50 to 250 psig can be maintained inside the reactor. Co-product hydrogen sulfide is thus continuously removed from the reaction zone. The progress of the reaction can be followed by monitoring the concentration of hydrogen sulfide in the purge gas thus indicating when to discontinue the heating and sparging. Secondary destruction of products by unnecessarily long reaction times is thus avoided.

It is highly desired to work with the ester derivatives, particularly the methyl ester derivatives, of stilbenedicarboxylic acids as compared with the free acid derivatives. For example, when trans 4,4'-stilbenedicarboxylic acid is formed using para-toluic acid, an elaborate isolation procedure is required to isolate the free acid derivative. Also a mixture of para-toluic acid and trans 4,4'-stilbenedicarboxylic acid sets up to a hard residue requiring xylene and KOH extraction to obtain the free acid derivative. In contrast, a mixture of methyl para-toluate and DMSDC is a slurry, requiring only simple filtration for isolation of DMSDC. In addition, for most applications, trans 4,4'-stilbenedicarboxylic acid must be purified via the acid chloride (which is an additional step). The acid chloride must then be converted to an ester derivative such as MSDC (still another step). In contrast, when working with an ester derivative of toluic acid as a starting material, such as methyl para-toluate, the corresponding stilbene ester deriviative, such as DNSDC, is formed directly which can be purified, if necessary, by simple recrystallization.

The novel compounds of the present invention (i.e., Compound I wherein R' is phenyl) can alternatively be prepared by ester interchange of the appropriate methyl ester stilbene derivatives (i.e., Compund I wherein R' is methyl) with phenyl acetate using a suitable catalyst such as dibutyltin oxide. After the stilbene phenyl ester derivative has been formed by this reaction, the reaction product typically contains the desired product, unreacted starting materials, excess catalyst and reaction by-products. It has been found that the desired product can be purified from such a reaction product by recrystallization using an appropriate solvent. It has been discovered that a particularly good solvent for this purpose is one which contains dimethylformamide (DMF).

The following examples are to illustrate the invention, but should not be interpreted as a limitation thereon.

EXAMPLE 1

Dehydrodimerization of Methyl p-Toluate to DMSDC

About 600 grams (4 mols) of methyl p-toluate (MPT) and 12.8 grams (0.4 mol) of sulfur (elemental) was added to a stirred, 1-liter autoclave designed to allow nitrogen flow through the reactor sufficient to remove the by-product $H_2S$ essentially as fast as it is formed. Exit of gases from the autoclave is through a condenser kept at 35° C. The autoclave was pressured with nitrogen to about 75 psig and the nitrogen flow was adjusted so that a steady flow passes through the liquid content of the autoclave at a rate of about 300 cc/min. The autoclave was then heated to a temperature of 280° C. and heating, stirring and nitrogen sparging were maintained until the hydrogen sulfide content of the off gas, as measured by an ultraviolet gas cell meter, was less than 0.1 vol. %. About 2 hours at 280° C. were required for this process. The reactor was then cooled and unloaded. On filtration at 45° C. and washing with methanol, 34.8 g (59.5% on MPT consumed) of dimethyl trans 4,4'-stilbenedicarboxylate (DMSDC) was obtained. The crude material assayed >98 mol % pure by NMR and contained 244 ppm sulfur (total) by x-ray fluorescence analysis. Additionally, the filtrate contained 9.12 g of dimethyl 4,4'-bibenzyldicarboxylate which may be isolated by high vacuum distillation and further converted to DMSDC by sulfur-promoted dehydrogenation for an efficient process. The DMSDC was recrystallized from methyl benzoate and melted at 230° C. to 233° C.

EXAMPLE 2

Dehydrogenation of Dimethyl 4,4'-Bibenzyldicarboxylate

A solution of the bibenzyl (dimethyl 4,4'-bibenzyldicarboxylate) in diphenyl ether was made up to give a near 1 M concentration of the bibenzyl. Enough sulfur was added to make the solution initially 0.1 M in sulfur and the solution was brought to 260° C. and sparged with inert gas at the rate of 1 SCFH per 150 mL of reactant solution. Sampling of the reaction mixture and gas chromotagraphic analysis showed that the concentration of DMSDC had reached 0.094 M by 480 minutes. The reaction mixture was cooled to 35° C. and the crystallized DMSDC product was isolated by filtration. The filtrate can be made up with additional bibenzyl and sulfur and recycled.

EXAMPLE 3

The effect of not removing the H₂S properly from the MPT/S reaction mixture can be seen by comparison of the DMSDC and corresponding bibenzyl yields in the following tabulated runs.

TABLE 1

Effect of H₂S Retention on Yields of Dimethyl Trans-4,4'-Stilbenedicarboxylate at 280° C.

| Experiment No. | Reactants, mols | | | N₂ Sparge | Products, moles | | DMSDC/ Bibenzyl (Mol Ratio) |
|---|---|---|---|---|---|---|---|
| | MPT[a] | S[b] | Ph₂O[c] | | DMSDC[d] | Bibenzyl[e] | |
| 071 | 2.0 | 0.2 | 2.0 | Yes | 0.0680 | 0.0110 | 6.18 |
| 134 | 2.0 | 0.2 | 2.0 | No | 0.0137 | 0.0905 | 0.151 |
| 079 | 4.0 | 0.2 | 0.0 | Yes | 0.0681 | 0.0117 | 5.82 |
| 198 | 4.0 | 0.2 | 0.0 | No | 0.0238 | 0.0819 | 0.291 |

[a]MPT = Methyl p-toluate
[b]S = Elemental sulfur
[c]Ph₂O = Diphenyl ester, an inert diluent and solvent.
[d]DMSDC = Dimethyl trans-4,4'-stilbenedicarboxylate.
[e]Bibenzyl = Dimethyl 4,4'-bibenzyldicarboxylate.
Other products besides the DMSDC and associated bibenzyl are formed in this reaction.

EXAMPLE 4

Table 2 illustrates the effect of varying molar ratios of reactants on combined yields of DMSDC and associated bibenzyl. All experiments in Table 2 were performed under N₂ sparge of varying rates.

TABLE 2

Effect of Conversion on Yields of Dimethyl Trans-4,4'-Stilbenedicarboxylate (DMSDC) at 280° C.

| Experiment No. | Reactants, Moles | | | MPT:S | Product, Millimoles | | | % Yield[g] (DMSDC + Bibenzyl) |
|---|---|---|---|---|---|---|---|---|
| | MPT[a] | S[b] | Ph₂O[c] | | DMSDC[d] | Bibenzyl[e] | Other[f] | |
| 079 | 4.00 | 0.200 | 0.00 | 20:1 | 68.1 | 11.7 | 9.3 | 84.6 |
| 073 | 4.00 | 0.400 | 0.00 | 10:1 | 116.9 | 30.6 | 30.9 | 75.1 |
| 037 | 4.00 | 0.800 | 0.00 | 5:1 | 179.8 | 89.0 | 43.7 | 78.8 |
| 087[i] | 4.00 | 1.000 | 0.00 | 4:1 | 123.0 | 53.5 | — | 37.3 |
| 110[h,i] | 1.04 | 0.258 | 1.04 | 4:1 | 88.3 | 23.6 | 104.2 | 47.3 |
| 126[h,i] | 1.04 | 0.258 | 1.04 | 4:1 | 121.1 | 42.1 | 87.8 | 63.0 |
| 071 | 2.00 | 0.200 | 2.00 | 10:1 | 68.0 | 11.0 | 9.9 | 83.3 |
| 119 | 2.00 | 0.1 | 2.00 | 20:1 | 39.8 | 6.1 | — | 81.1 |

[a]MPT = Methyl p-toluate
[b]S = Elemental sulfur
[c]Ph₂O = Diphenyl ester, an inert diluent and solvent.
[d]DMSDC = Dimethyl trans-4,4'-stilbenedicarboxylate.
[e]Bibenzyl = Dimethyl 4,4'-bibenzyldicarboxylate.
[f]Side products include a benzothiophene, tetrakis (4-carbomethoxyphenyl) thiophene, 1,2,3-tris(4-carbomethoxyphenyl)propane and 1,2,3-tris(4-carbomethoxyphenyl)propene.
[g]Yield based on MPT consumed.
[h]Reaction temperature = 300° C.
[i]Not an example of the present invention.

As can be seen from Table 2, low values of MPT/S also tend to promote formation of the bibenzyl over the stilbene product.

EXAMPLE 5

Preparation of DPSDC

Two hundred twelve g (1.00 mole) of phenyl p-toluate and 340 g of diphenyl ether were heated to 280° C. with 3.20 g (0.10 mole) of sulfur in an autoclave at a maintained pressure of 100 psig with a nitrogen purge of about 2 standard cubic feet per hour. After about 2 hours the evolution of hydrogen sulfide, as measured in the nitrogen purge gas stream, had ceased and the reactor was allowed to cool. The reaction product mixture was filtered at 45° C. to yield 420.6 g of filtrate (mixture of diphenyl ether and reacted phenyl p-toluate) and 110.8 g of solid (product and unreacted phenyl p-toluate). The solid on the filter funnel was washed with several 100 mL portions of acetone to yield, after drying, 14.0 g of diphenyl 4,4'-stilbenedicarboxylate. An additional 0.46 g of product was obtained by acetone rinse of the reactor vessel; the total yield, 14.46 g, is 68.8% of the theoretical based on the sulfur consumed. The combined products were recrystallized from cyclohexanone to give 13.2 g of light yellow product, mp. 227°–229° C. The NMR spectrum (70% CDCl3, 30% trifluoroacetic acid) of the product was in accord with the proposed structure: $\delta$. 8.28(d,4H), 7.75(d,4H), 7.48(t,4H), 7.35(m,4H), 7.20(d,4H).

EXAMPLE 6

Preparation of DPSDC

Phenyl acetate (204.3 g, 1.5 mole) was charged to a 1-liter, 3-neck flask equipped with a magnetic stirrer, a distillation column, and a distillation head. The phenyl acetate was heated to 200° C. and dibutyltin oxide (1.0 g) was added while stirring. DMSDC (148.1 g, 0.50 mole) was then added portionwise to the mixture. All materials were in solution as the temperature approached 200° C. The solution was stirred for about 6 hours at 205°–208° C. while methyl acetate was collected overhead as it was formed. After standing overnight at 180° C., the reaction mixture was reheated to 224° C. and held there for an additional 8.5-hour period during which time methyl acetate was collected; a total of 68.9 g of low boilers were collected. The reaction product was poured into a baking dish wherein the liquid solidified almost immediately. The solidified material was then ground with a mortar and pestle and slurried with cold DMF. The material was collected by filtration, washed with acetone and air dried (Yield: 182 g).

The crude product was recrystallized from hot DMF with a solvent/solute ratio of about 10:1. Crystals were precipitated by the cooling bright yellow DMF solution and were collected by filtration, washed with cold DMF than with acetone, and air dried. The solid was pale yellow (Yield: 177.4 g, M.P. 221°–223° C.). Gas chromatography confirmed the purity of the desired product as greater than 99%.

EXAMPLE 7

Preparation of DPSDC

Sixty five g (0.306 mole) of neat phenyl p-toluate were maintained in the temperature range of 280°–310° C. (boiling point) while a slow stream of nitrogen was bubbled in from below the surface (sparged). Sulfur (1.92 g, 0.060 mole) dissolved in more phenyl p-toluate (20 g, 0.099 mole) at 100° C. was added slowly with stirring over a period of 2–3 hours. The heating, stirring and nitrogen sparging were continued an additional four hour and then the mixture was allowed to cool near 80° C. and 100 mL of boiling acetone was added. The suspension was transferred to a larger flask and an additional 400 mL of acetone was added. The suspension was filtered at the boil to yield 3.8 g of diphenyl 4,4'-stilbenedicarboxylate.

We claim:

1. An ester compound of the formula:

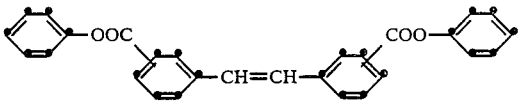

wherein the

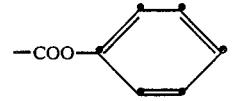

moieties are bonded at the meta or para positions.

2. The compound of claim 1 which is diphenyl trans-4,4'-stilbenedicarboxylate.

* * * * *